United States Patent [19]

MacGregor

[11] Patent Number: 4,880,002
[45] Date of Patent: Nov. 14, 1989

[54] STRETCHABLE POROUS SUTURES

[75] Inventor: David C. MacGregor, Miami, Fla.

[73] Assignee: Corvita Corporation, Miami, Fla.

[21] Appl. No.: 130,746

[22] Filed: Dec. 9, 1987

Related U.S. Application Data

[63] Continuation-in-part of Ser. No. 839,545, May 30, 1985, Pat. No. 4,712,553, and a continuation-in-part of Ser. No. 54,750, May 27, 1987.

[51] Int. Cl.⁴ .............. A61L 17/00; A61B 17/06; C08J 9/26
[52] U.S. Cl. .......................... 335.5; 128/339; 521/61
[58] Field of Search .............. 128/335.5, 339

[56] References Cited

U.S. PATENT DOCUMENTS

| | | | |
|---|---|---|---|
| 1,337,480 | 4/1920 | Matthaei | 128/339 |
| 2,940,247 | 6/1960 | Kirshbaum | 128/335.5 |
| 3,094,123 | 6/1963 | Kurtz | 128/339 |
| 3,130,728 | 4/1964 | Pearson | 128/335.5 |
| 3,187,752 | 6/1965 | Glick | 128/335.5 |
| 3,317,924 | 5/1967 | Le Veen | 623/1 |
| 3,791,388 | 2/1974 | Hunter | 128/335.5 |
| 3,847,156 | 11/1974 | Trumble | 128/335.5 |
| 3,870,593 | 3/1975 | Elton et al. | 521/61 |
| 3,918,455 | 11/1975 | Coplan | 128/339 |
| 3,953,566 | 4/1976 | Gore | 264/505 |
| 3,992,725 | 11/1978 | Homsy | 623/11 |
| 4,043,344 | 8/1977 | Landi | 128/335.5 |
| 4,044,404 | 8/1977 | Martin et al. | 623/1 |
| 4,096,227 | 6/1978 | Gore | 264/110 |
| 4,101,984 | 7/1978 | MacGregor | 128/92 YG |
| 4,110,392 | 8/1978 | Yamazaki | 264/127 |
| 4,116,738 | 9/1978 | Pall | 156/167 |
| 4,173,689 | 11/1979 | Lyman et al. | 521/64 |
| 4,355,426 | 10/1982 | MacGregor | 623/1 |
| 4,385,093 | 5/1983 | Hubis | 428/316.6 |
| 4,459,252 | 7/1984 | MacGregor | 264/46.9 |
| 4,475,972 | 10/1984 | Wong | 156/167 |

OTHER PUBLICATIONS

Leidner et al, "A Novel Process for the Manufacturing of Porous Grafts: Process Description and Product Evaluation," *Journal of Biomedical Materials Research*, vol. 17, pp. 229-247.

W. L. Gore and Associates, Inc., *Investigating Surgeons Brochure Gore-Tex Expanded PTFE Suture.*

*Primary Examiner*—Edward M. Coven
*Assistant Examiner*—Gary Jackson
*Attorney, Agent, or Firm*—Lockwood, Alex, Fitzgibbon & Cummings

[57] ABSTRACT

Surgical sutures are provided that have an elastomeric and porous structure. The elastomeric porous structure can be formed from a plurality of fibers that are wound onto a stylet or onto an elongated and elastomeric central core of the suture, or from a mixture including elutable material that is cast into the configuration of a suture, either as a generally unitary cylinder or over an elongated and elastomeric central core of the suture.

14 Claims, 3 Drawing Sheets

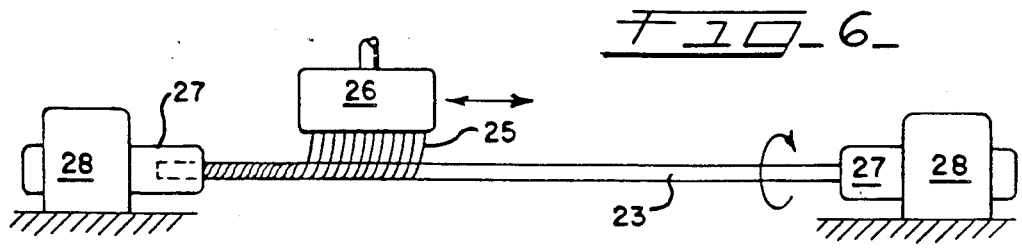
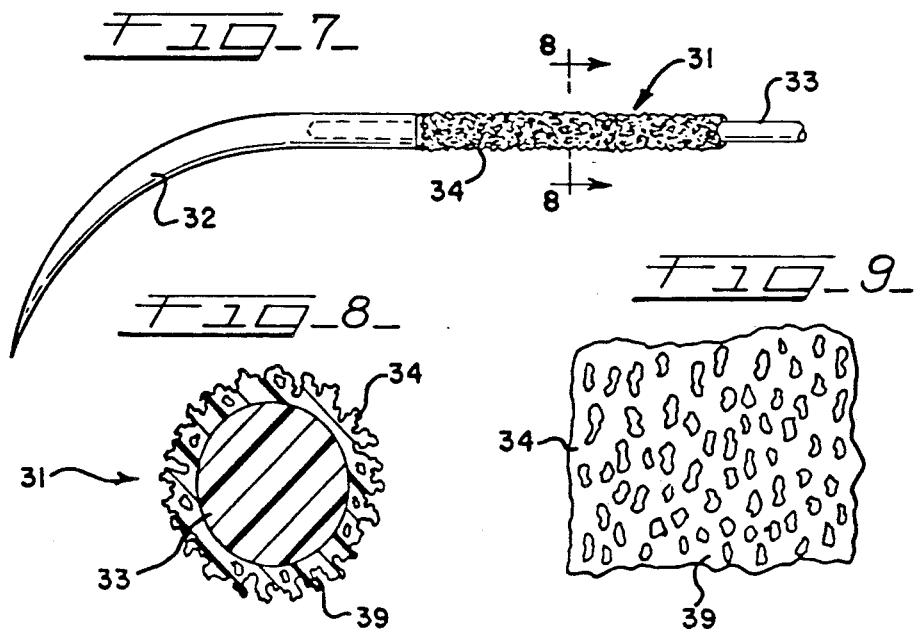
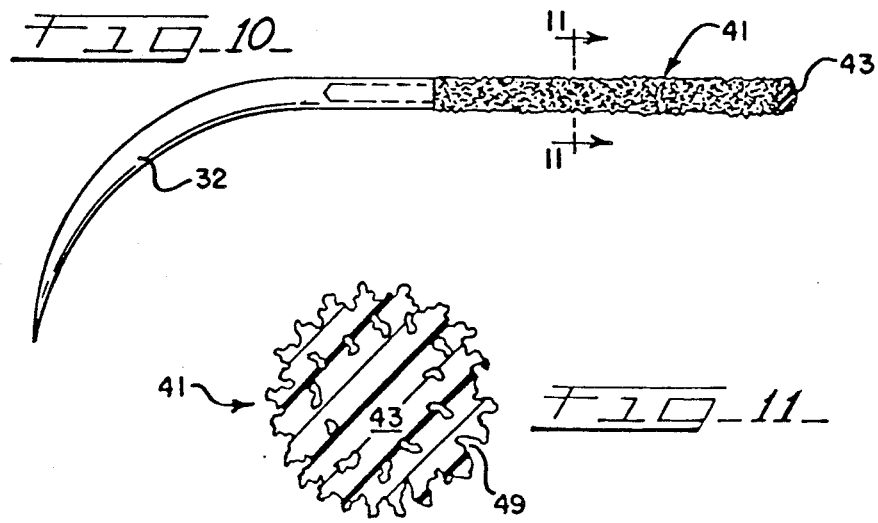

STRETCHABLE POROUS SUTURES

BACKGROUND AND DESCRIPTION OF THE INVENTION

This application is a continuation-in-part of application Ser. No. 739,545, filed May 30, 1985 (U.S. Pat. No. 4,712,553) and of application Ser. No. 054,750, filed May 27, 1987.

The present invention generally relates to surgical sutures that are stretchable and that have a porous structure, the suture being of the non-braided and non-woven type and having a surface porosity that provides an environment that is conducive to tissue ingrowth into the pores of the porous surface. The porous surface may be formed from a plurality of elastomeric fibers that are wound onto a mandrel or onto an elongated elastomeric filament and onto themselves while providing adequate spacing therebetween so as to form a surface having pores of the desired size. Alternatively, the porous surface can be formed from a mixture of elastomeric polymer and elutable materials, which mixture is cast into the configuration of a suture, after which the elutable material is eluted in order to form the porous surface of the stretchable suture.

Most sutures which are available today for the repair, fixation and/or approximation of body tissues during surgical procedures are composed of single strands or multiply braided strands of flexible material, with or without a needle attached to one or both ends of the flexible material. Sutures which are used for the attachment of prosthetic devices or implants to body tissues have especially stringent requirements regarding strength, biocompatibility, flexibility, sterilizability and, in some cases, biodegradability. An especially desirable property for sutures that are intended for specialized uses such as those involving biologic, synthetic or biosynthetic vascular grafts is to provide the suture with porosity that extends to the external surface of the suture and that provides for rapid tissue ingrowth and endothelialization, as well as other important properties.

Providing prosthetic devices and implants with porous surfaces has been developed during the last few years in order to promote the implantation of such devices. Porous coatings or surfaces have been implemented on or proposed in connection with devices such as heart valves, cardiac pacers and electrodes thereof, vascular grafts, blood pumps, ventricular assist devices, artificial hearts, flexible heart valve members, bloodstream filters, intracardiac patches, diaphragms or baffles, vascular access tubes, and the like. One of the objectives of providing porous surfaces on these types of devices and implants is to promote colonization and tissue ingrowth into the depth of the porous surface from adjacent body tissue in order to provide bonding between the body tissue host and the porous member. Typically, the body tissue ingrowth is combined with the promotion of tissue growth into the porous surface from the nucleated bloodstream cells. Such porous surfaces provide a porous depth that affords a means of fixation to host tissues by soft tissue growth into the porous depth of the surface, and they provide tissue-implant interfaces which are blood compatible arising from colonization and tissue formation on the blood-contacting surfaces.

Imparting stretching and porosity to sutures according to the present invention has been found to provide advantageous properties including exceptional compliance between the host tissue and the implant, device or the like while simultaneously permitting body tissue ingrowth into the pores of the suture in order to accelerate the healing process. The property of exceptional compliance of the stretchable suture assists the suture in being able to yield to bending under stress conditions imparted by sewn and/or knotted suture assemblies. By allowing tissue ingrowth into the interstices of the porous suture, potential dead spaces are reduced or eliminated thus making the suture less prone to primary or secondary infection. The stretchable porous suture also provides the possibility for reduced intimal hyperplasia and stenotic narrowing at the anastomotic site. The generally compressible nature of the stretchable porous suture permits the use of a needle whose diameter is less than that of the suture itself in order to thereby reduce blood leakage at suture sites in vascular anastomoses.

Additionally, the elastomeric properties and surface irregularities that are associated with the stretchable porous suture structure according to this invention result in less slippage when the suture is tied in order to provide a more secure knot than that achieved by using smooth or monofilament sutures that are not elastomeric. The porous suture structure also provides a favored environment for the controlled release of drugs to promote healing and/or to resist infection. Porous stretchable sutures according to this invention can be made of the same material as, and be provided with a surface structure that is similar to, the device being implanted with the aid of the suture, such as a synthetic graft, with the result that the suture material will demonstrate substantially the same physical and chemical properties as the device being sutured. This can be of assistance in promoting more uniform healing because the surface free energy of the porous suture will be similar to that of the graft being secured thereby. If desirable, the porous suture can be bonded to the vascular graft or the like, which is facilitated when the suture and the graft are made of substantially the same material.

These various properties and advantages have been attained by the present invention, by which a non-braided stretchable surgical suture is provided which includes an exterior portion having a porous structure, such exterior portion being between the outer surface of the suture and a location internal thereof to provide a porous surface or layer. The porous stretchable suture may be formed by winding spun fibers or by elution techniques. This porous surface or layer may be formed over a mandrel or over a generally continuous elongated elastomeric core member by the winding or the elution procedure, or it may be formed by elution from a continuous elongated polymeric member. In any case, the suture, including its porous surface or layer, is constructed of a polymeric material that exhibits substantial elastomeric properties.

It is accordingly a general object of the present invention to provide an improved surgical suture.

Another object of this invention is to provide an improved surgical suture that has a porous surface, coating or layer external thereof.

Another object of the present invention is to provide an improved surgical suture that is of the non-braided, non-woven type, while still having compressible qualities for reducing blood leakage at suture sites in vascular anastomoses.

Another object of the present invention is to provide an improved surgical suture that permits body tissue ingrowth into an external portion thereof that provides a porous surface.

Another object of this invention is to provide an improved porous surgical suture for accelerating the healing process and for reducing the likelihood of primary or secondary infection.

Another object of the present invention is to provide an improved surgical suture that can be made from the same material and can be provided with the same surface structure as a synthetic graft or the like that is being fixed in place by the suture.

Another object of this invention is to provide an improved surgical suture that is provided with surface irregularities that lessen the likelihood of slippage when the suture is tied and that provide a favored environment for the controlled release of drugs to promote healing and/or to resist infection.

Another object of the present invention is to provide an improved surgical suture that is stretchable, particularly in the axial direction.

Another object of this invention is to provide an improved surgical suture that exhibits improved matching of compliance between host tissue and a graft or the like.

These and other objects, features and advantages of this invention will be clearly understood through a consideration of the following detailed description.

BRIEF DESCRIPTION OF THE DRAWINGS

In the course of this description, reference will be made to the attached drawings, wherein:

FIG. 6 is a generally schematic sketch showing a step in the manufacture of stretchable and porous sutures such as are illustrated in FIGS. 1 through 5;

FIG. 7 is a broken away elevational view of another embodiment of the stretchable porous suture in accordance with this invention;

FIG. 8 is a cross-sectional view along the line 8—8 of FIG. 7;

FIG. 9 is an illustration of the stretchable and porous surface of the embodiment of FIGS. 7 and 10;

FIG. 10 is an elevational view, partially broken away, of a further and generally preferred embodiment of the stretchable, porous suture in accordance with this invention;

FIG. 11 is a cross-sectional view along the line 11—11 of FIG. 10;

DESCRIPTION OF THE PARTICULAR EMBODIMENTS

Figure 1:
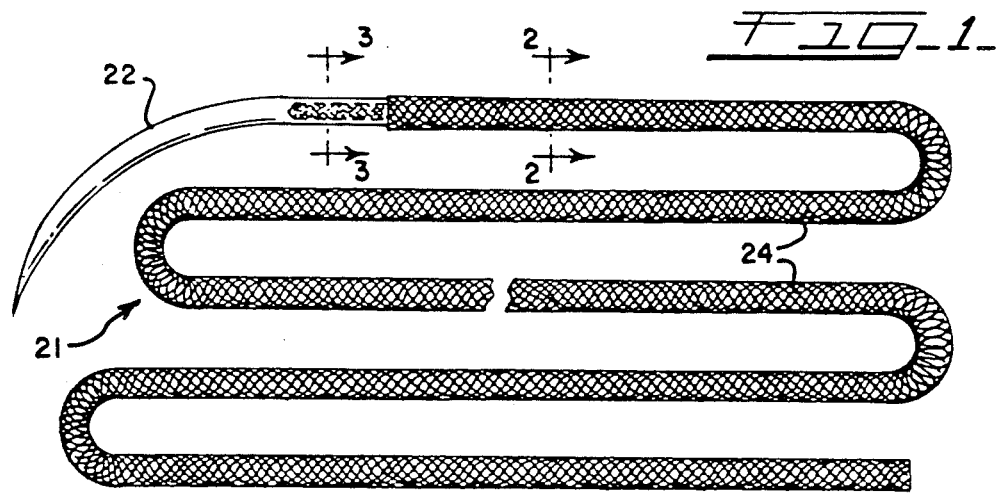
FIG. 1 is an elevational view of a stretchable porous suture in accordance with this invention.

An assembly of a length of suture material, generally designated as 21, and a suture needle 22 is illustrated in FIG. 1. Needle 22 is attached to the suture material 21 by crimping, swaging or the like. Preferably, the suture needle 22 has an outside diameter that is smaller than the uncompressed outside diameter of the suture material 21 in order to assist in reducing or preventing leakage along the suture line during and after surgery, this feature being possible in large measure due to the radial compressibility of the elastomeric suture material 21.

With more particular reference to the suture material that is illustrated in FIGS. 2, 3, 5 and 13, such includes an elastomeric support 23 and a generally cylindrical elastomeric and porous elongated portion 24 or 24a which is in the form of a generally cylindrical elongated porous polymeric surface or sheath that has an inside diameter which is substantially the same as the outside diameter of the support 23 so that the stretchable, porous portion or layer 24 or 24a closely overlies and is substantially attached to the stretchable support 23 by virtue of a close-fitting relationship or by heat or solvent bonding.

Figure 2:
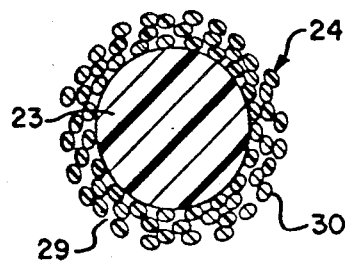
FIG. 2 is a cross-section along the line 2—2 of FIG. 1.
Figure 3:
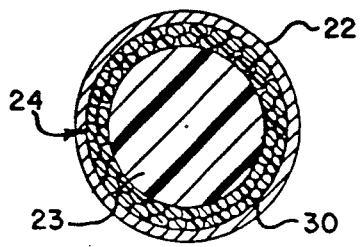
FIG. 3 is a cross-section along the line 3—3 of FIG. 1.

Support 23 may be a monofilament as illustrated in FIGS. 2 or 3, or same can be composed of a plurality of filaments (not shown). Porous, elastomeric portion or sheath 24 (as illustrated in more detail in FIGS. 12 and 13) and porous elastomeric portion or sheath 24a (FIGS. 4 and 5) are each composed of a plurality of elastomeric polymer fibers that are generally spun onto the support 23 so as to form pores 29. A suitable spinning technique is illustrated in FIG. 6 in conjunction with an apparatus that extrudes one or more filaments 25 onto a secured support 23, such as a polymeric central core or a stylet which is removed after manufacturing has been completed.

Regarding the apparatus illustrated in FIG. 6, such includes a spinnerette or distributor 26 for directing the filaments 25, typically in conjunction with formation of those filaments by extrusion techniques, onto the central core or stylet 23 which is held under tension by suitable jaws 27. In the arrangement illustrated in FIG. 6, the distributor 26 moves back and forth within a plane generally between the jaws 27, while the central core or stylet secured support 23 is rotated by suitable means such as the illustrated motors 28. Alternatively, the distributor 26 can take the form of a spinnerette that rotates around the tensioned secured support 23. Whatever mechanism or technique is utilized, same will result in combined rotational and translational relative movement between the secured support 23 and the filaments 25.

Numerous layers of stretchable polymeric fibers can be laid down from the filaments 25 over the secured support 23, the number of layers being dependent upon the desired outer diameter size of the suture material 21. On the order of 1000 filament passes can be typical. Sizes of suture material 21 can range between that of a 12-0 U.S.P. size suture having an outer diameter as small as 0.001 mm and a U.S.P. size 2 suture having an outer diameter as large as about 0.599 mm. Thus, suture material 21 may have an outside diameter between about 0.001 mm and about 0.6 and above, depending upon the desired suture use.

Typical sizes of suture material 21 according to this invention include a 7-0 suture material having a diameter of between about 0.050 and 0.069 mm, while the diameter of a 6-0 suture material is on the order of polymeric fiber can have a diameter ranging between about 0.001 to 0.020 mm, typically on the order of about 0.005 mm, in order to form a porous coating 24 or 24a having a thickness between about 0.010 and about 0.200 mm, preferably between about 0.050 and about 0.150 mm. The average size of each pore 29 is on the order of about 0.005 and about 0.060 mm.

In a specific example, 6-0 suture material according to this invention has a secured support 23 that is an elastomeric polymer central core having a diameter of between about 0.020 and about 0.049 mm, while the elastomeric porous polymeric coating 24 or 24a has a thickness of about 0.050 mm, being made up of 0.005 mm stretchable polymeric fibers that are laid down in a maximum of about 2000 filament passes to form a porous coating 24 or 24a having the total thickness of about 0.050 mm. The number of revolutions needed to lay down these filament passes depends primarily upon the number of nozzles on the spinnerette or distributor 26. In this example, the spacing between each polymeric fiber is so chosen to provide pores 29 having an average size of approximately 0.025 mm. Such porosity is determined by the diameter of the polymeric fibers, the closeness of these fibers to each other when wound, the number of layers of such polymeric fibers, and the extent that adjacent ones of such fibers fuse together.

Figure 4:
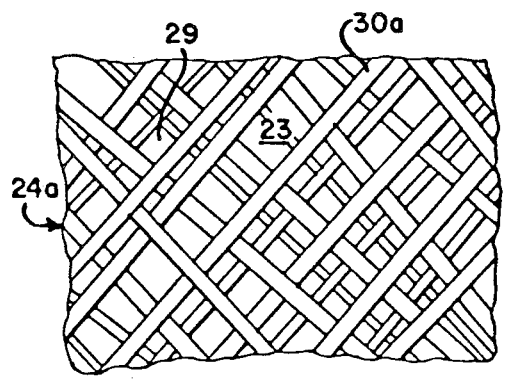
FIG. 4 is a sketch of a porous coating and stretchable suture according to the invention at a magnification on the order of 150 times.
Figure 5:
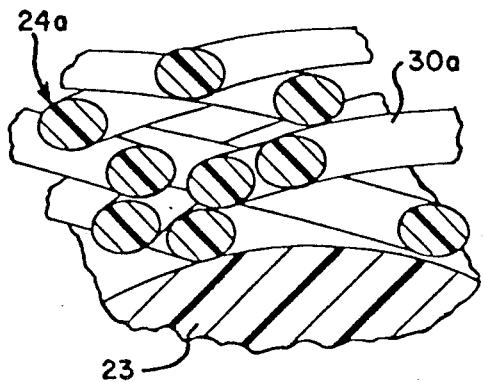
FIG. 5 is a sketch of an edge of a porous and stretchable suture according to the invention at an approximate magnification of 1000 times.

With specific reference to the embodiment of the porous coating 24a that is illustrated in FIGS. 4 and 5, the filaments 25 are spun so that they are laid down as stretchable polymeric fibers 30a onto the secured support 23 and onto each other in a manner by which each polymeric fiber 30a maintains its generally cylindrical configuration throughout its length. Where the fibers 30a generally cross each other in the FIGS. 4 and 5 embodiment, they only slightly modify their respective generally cylindrical shapes to form the porous coating 24a.

Figure 12:
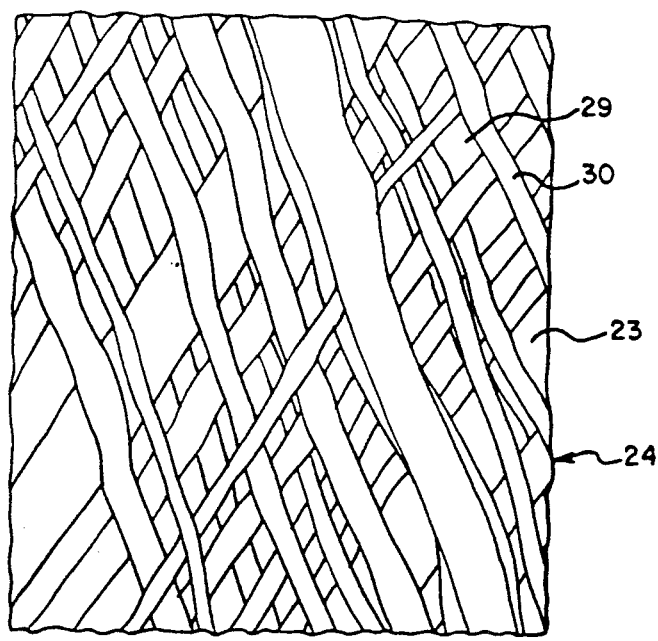
FIG. 12 is a sketch of a detailed and enlarged view of a stretchable porous suture generally according to FIG. 4.
Figure 13:
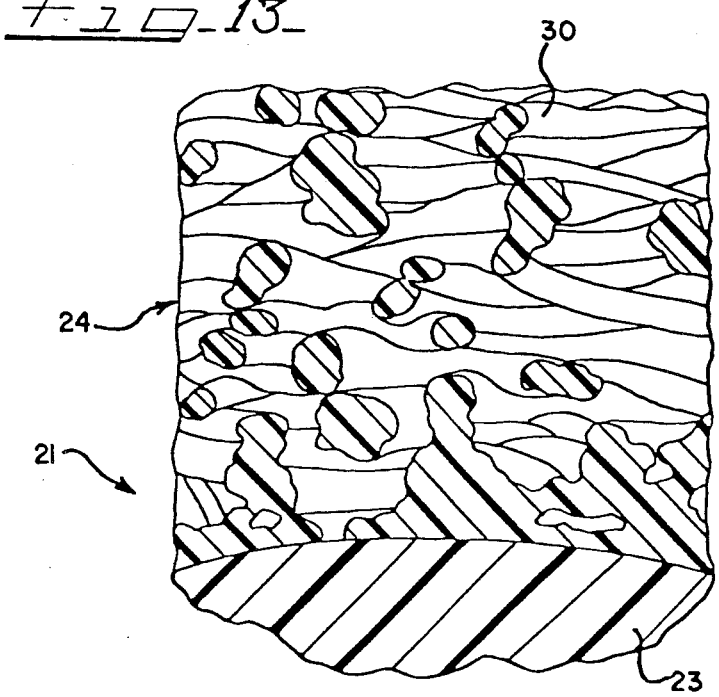
FIG. 13 is a sketch of a detailed and enlarged view of a stretchable suture generally according to FIG. 5.

Enhanced strength over that experienced by the suture having a porous coating 24a is imparted to the porous suture by providing the porous coating 24 illustrated in FIGS. 12 and 13. In this embodiment, individual polymeric fibers 30 are laid down when they are in a softened, substantially plastic state, whereby they deform from their respective generally cylindrical configurations, especially at those locations where they cross over or otherwise engage one another. Such deformed polymeric fibers 30 are generally S-shaped along their length and tend to exhibit complementary and oppositely oriented indents at those locations where adjacent fibers 30 cross one another. As a result, each subsequent layer of the fibers 30 generally "sinks" toward the secured support 23 and generally drapes over the layer of fibers 30 lying thereunder. The deformability or plasticity needed to thus form these polymeric fibers 30 is typically achieved by extruding the filaments 25 in a manner by which their hardening is delayed, for example by being accompanied by excess or residual solvent.

Other embodiments, such as those illustrated in FIGS. 7, 8, 9, 10 and 11, do not incorporate filaments in this same manner. The porosity of the suture material of those embodiments is determined by the size of elutable materials which may be solvents for the polymer or particles such as salts, as well as by the concentration of those elutable materials that can be expressed as a percent by volume of a pre-elution mixture thereof with the polymer of the suture material. These embodiments incorporate an elution technique for forming an elastomeric porous suture material 31 or 41 which may, if desired, be attached to a suture needle 32 by crimping or swaging.

In the embodiment illustrated in FIGS. 7 and 8, the suture material 31 includes a stretchable polymeric central core 33 and porous coating 34. The porous coating 34 is formed by applying, over the central core 33, a mixture of an elastomeric polymeric material and elutable material such as a solvent or salt granules, after which the elutable material is dissolved out to form a plurality of pores 39. This mixture of polymeric material and elutable material may be extruded onto the central core 33 by available extrusion devices so that the mixture surrounds and forms a sheath-like surface over the central core 33.

Alternatively, as illustrated in FIGS. 10 and 11, the mixture of polymeric material and elutable material may be extruded as a solid cylinder. Subsequent elution of this solid cylinder forms the stretchable, porous suture material 41 which has a central core 43 that is integral with and that is a continuous, unitary portion of the polymeric material that surrounds the central core 43 and that includes eluted pores 49. With this embodiment, there is no need to secure a porous coating to a separate central core by force fitting, heat bonding, adhesive bonding or the like.

Porous suture material 41 is a stretchable and flexible non-metallic elastomeric material that is either inert or biodegradable. Suitable polymeric materials are axially stretchable to a substantial extent, typically up to about twice its initially extruded length, or more. These materials may include polyurethanes, polycarbonates and various copolymers. Polyurethanes are preferred because of their biocompatibility, superior elastomeric properties and flexibility. Satisfactory elutable materials include solvents for the particular polymer that is used, as well as particles such as salts, including sodium chloride crystals, sodium carbonate, calcium fluoride and magnesium sulfate. Elutable materials are water-soluble materials that are readily leached by the utilization of water as the elution medium. Other materials that are soluble in organic solvents and the like can be substituted as desired.

In those embodiments that utilize a suture material that is an assembly of a separate central core and a porous coating, both components of the suture material may be made of the same elastomeric material, or they may be made of differing materials depending upon the particular objective to be achieved. For example, there might be a desire to have the porous coating constructed of the same material as the prosthetic device or graft that is to be sutured by the elastomeric and porous suture, while it might be desirable to provide an initially separate central core of that same suture material which is especially elastomeric or flexible or which has a particularly high tensile strength or which possesses some other highly desirable property for a particular use.

It will be understood that the embodiments of the present invention which have been described are illustrative of some of the applications of the principles of the present invention. Numerous modifications may be made by those skilled in the art without departing from the true spirit and scope of the invention.

I claim:

1. A non-braided surgical suture, comprising: a suture material including:

an elongated flexible, non-metallic generally cylindrical member having a plurality of pores, said porous elongated flexible member being elastomeric and being a generally cylindrical and flexible extrudate of a mixture of polymeric material and elutable material, said extrudate having been subjected to elution of said elutable material from said polymeric material to thereby form said pores of the porous elongated flexible and elastomeric member, said polymeric material being selected from the group consisting of polyurethanes and polycarbonates;

said elongated flexible and elastomeric member has an initially extruded length and is axially stretchable up to about twice its said initially extruded length or more, whereby said suture is compliant with host tissue when it is implanted; and said elongated flexible and elastomeric member has an external diameter that is no larger than that of a surgical suture and a porous surface that promotes a tissue ingrowth into said porous elongated flexible member.

2. The surgical suture according to claim 1, wherein said plurality of pores have a pore size of on the order of about 0.005 and about 0.06 mm.

3. The surgical suture according to claim 1, further including a needle member attached to a radially compressed end portion of said suture material.

4. The surgical suture according to claim 3, wherein said needle member has an outside exposed diameter that is smaller than said external diameter of the elongated flexible member.

5. The surgical suture according to claim 1, wherein said external diameter of the elongated flexible member is no greater than about 0.6 mm.

6. The surgical suture according to claim 1, wherein said elongated flexible member is made of a polyurethane.

7. A non-braided surgical suture, comprising:

a suture material including: an elongated flexible, non-metallic generally cylindrical and elastomeric polymeric member having an initial, unstretched length and a plurality of pores, said elongated flexible and elastomeric member being a polyurethane or a polycarbonate having a plurality of pores has an external diameter that is no larger than that of a surgical suture, has a porous surface that promotes tissue ingrowth into said porous elongated flexible member, and is axially stretchable to a substantial extent beyond its said initial unstretched length, whereby said suture is compliant with host tissue when it is implanted; and a needle member attached to a radially compressed end portion of said elastomeric and porous suture material.

8. The non-braided surgical suture according to claim 7, wherein said generally cylindrical and elastomeric polymeric member having a plurality of pores includes a plurality of wound spun fibers that are wound one onto another into multiple layers of fibers.

9. The non-braided surgical suture according to claim 8, wherein said plurality of spun fibers are heat bonded to each other.

10. The non-braided surgical suture according to claim 8, wherein said plurality of spun fibers are solvent bonded to each other.

11. 14. The non-braided surgical suture according to claim 7, wherein said generally cylindrical and elastomeric polymeric member having a plurality of pores had been formed by eluting elutable material from an extruded mixture of elastomeric polymeric material and elutable material.

12. The non-braided surgical suture according to claim 7, wherein said needle member has an exposed outside diameter that is smaller than said outside diameter of said generally cylindrical porous polymeric and elastomeric member that is radially uncompressed.

13. The non-braided surgical suture according to claim 7, wherein said generally cylindrical porous polymeric and elastomeric member has an outside diameter of between about 0.001 mm and about 0.6 mm and above.

14. The non-braided surgical suture according to claim 7, wherein said suture material is made of a polyurethane.

* * * * *

UNITED STATES PATENT AND TRADEMARK OFFICE
CERTIFICATE OF CORRECTION

PATENT NO. : 4,880,002
DATED : November 14, 1989
INVENTOR(S) : David C. MacGregor It is certified that error appears in the above-indentified patent and that said Letters Patent is hereby corrected as shown below:

On the cover page, under "Related U.S. Application Data", line 1, "Ser. No. 839,545" should read --Ser. No. 739,545--; under "References Cited", "U.S. Patent Documents", Pat. No. 3,992,725, the date should read --11/1976--.
Col. 5, line 2, after "on the order of" insert --between about 0.070 and 0.099mm. Each stretchable--.
Col. 7, line 30, delete "outside exposed" and insert --exposed outside--.
Col. 8, line 24, delete "14.".

Signed and Sealed this

First Day of October, 1996

Attest:

BRUCE LEHMAN

*Attesting Officer*  *Commissioner of Patents and Trademarks*